US012758575B2

(12) United States Patent
Ballet et al.

(10) Patent No.: US 12,758,575 B2
(45) Date of Patent: Oct. 13, 2026

(54) GLYCOSIDE INHIBITORS OF YEAST

(71) Applicants: LESAFFRE ET COMPAGNIE, Paris (FR); UNIVERSITÉ CLERMONT AUVERGNE, Clermont Ferrand (FR); UNIVERSITE DE LILLE, Lille (FR); CENTRE NATIONAL DE LA RECHERCHE SCIENTIFIQUE—CNRS, Paris (FR)

(72) Inventors: Nathalie Ballet, Marcq en Baroeul (FR); Pascal Vandekerckove, Villeneuve d'Ascq (FR); Yann Guerardel, Ronchin (FR); Shin-Yi Yu, Lille (FR); Adeline Sivignon, Gerzat (FR); Nicolas Barnich, Madriat (FR)

(73) Assignees: LESAFFRE ET COMPAGNIE, Paris (FR); UNIVERSITÉ CLERMONT AUVERGNE, Clermont Ferrand (FR); UNIVERSITE DE LILLE, Lille (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 448 days.

(21) Appl. No.: 18/550,349

(22) PCT Filed: Mar. 15, 2022

(86) PCT No.: PCT/FR2022/050459

§ 371 (c)(1),
(2) Date: Sep. 13, 2023

(87) PCT Pub. No.: WO2022/195212

PCT Pub. Date: Sep. 22, 2022

(65) Prior Publication Data

US 2024/0148778 A1 May 9, 2024

(30) Foreign Application Priority Data

Mar. 16, 2021 (FR) ...................................... 2102618

(51) Int. Cl.

| | |
|---|---|
| ***A61K 31/716*** | (2006.01) |
| ***A61K 36/064*** | (2006.01) |
| ***A61P 31/04*** | (2006.01) |

(52) U.S. Cl.

CPC .......... *A61K 31/716* (2013.01); *A61K 36/064* (2013.01); *A61P 31/04* (2018.01)

(58) Field of Classification Search

None

See application file for complete search history.

(56) References Cited

U.S. PATENT DOCUMENTS

| | | | | |
|---|---|---|---|---|
| 5,663,061 A * | 9/1997 | Broker | C12N 15/815 435/254.2 |
| 5,663,324 A * | 9/1997 | James | A61K 31/716 536/123 |
| 9,750,762 B2 * | 9/2017 | Laville | A61P 3/08 |
| 2004/0014715 A1 * | 1/2004 | Ostroff | A61K 39/395 514/54 |
| 2012/0258930 A1 * | 10/2012 | O'Sullivan | A61P 43/00 514/54 |

FOREIGN PATENT DOCUMENTS

| | | | | |
|---|---|---|---|---|
| FR | 2928652 A1 | 9/2009 | |
| FR | 3089788 A1 | 6/2020 | |
| JP | H06107702 A | 4/1994 | |
| JP | H11501691 A | 2/1999 | |
| JP | 2011509651 A | 3/2011 | |
| WO | WO-9826787 A1 * | 6/1998 | A61P 1/00 |
| WO | 2009103884 A2 | 8/2009 | |
| WO | 2020079641 A1 | 4/2020 | |

OTHER PUBLICATIONS

International Search Report issued on Jun. 9, 2022, in corresponding PCT Patent Application No. PCT/FR2022/050459, 8 pages.
Alugongo et al., "Review: Utilization of yeast of origin in artificially raised calves", Journal of Animal Science and Biotechnology, Biomed Central Ltd, London, UK, vol. 8, No. 1, May 1, 2017, p. 1-12, XP021244599, 12 pages.
Roussel et al., "Anti-infectious properties of the probiotic *Saccharomyces cerevisiae* CNCM I-3856 on enterotoxigenic *E. coli* (ETEC) strain H10407", May 25, 2018, vol. 102, No. 14, pp. 6175-6189, XP036531450, 15 pages.
Samuelsen et al., "Effects of orally administered yeast-derived beta-glucans: A review", Jan. 1, 2014, vol. 58, No. 1, p. 183-193, XP002733985, 11 pages.
Office Action issued on Feb. 10, 2026, in corresponding Japanese Application No. 2023-554878, 10 pages.

* cited by examiner

*Primary Examiner* — Dale R Miller
(74) *Attorney, Agent, or Firm* — Maier & Maier, PLLC

(57) ABSTRACT

A composition of yeast polysaccharides including β(1,6)-glucans, preferably also mannans and α-glucans. The yeast polysaccharides are extracted from yeast cell wall fragments. Typically, the β-glucans are β(1,6)-glucans. Also, a method for obtaining such a composition, including at least one step of fractionating a composition of yeast cell walls and extracting an insoluble fraction, and at least one step of extracting a soluble fraction from the insoluble fraction obtained in step a). Further, a composition with a human or veterinary therapeutic objective, for the treatment of gastro-intestinal pathologies associated with pathogenic microorganisms, as well as to its non-therapeutic use for improving intestinal comfort.

16 Claims, 12 Drawing Sheets

[Fig. 1]
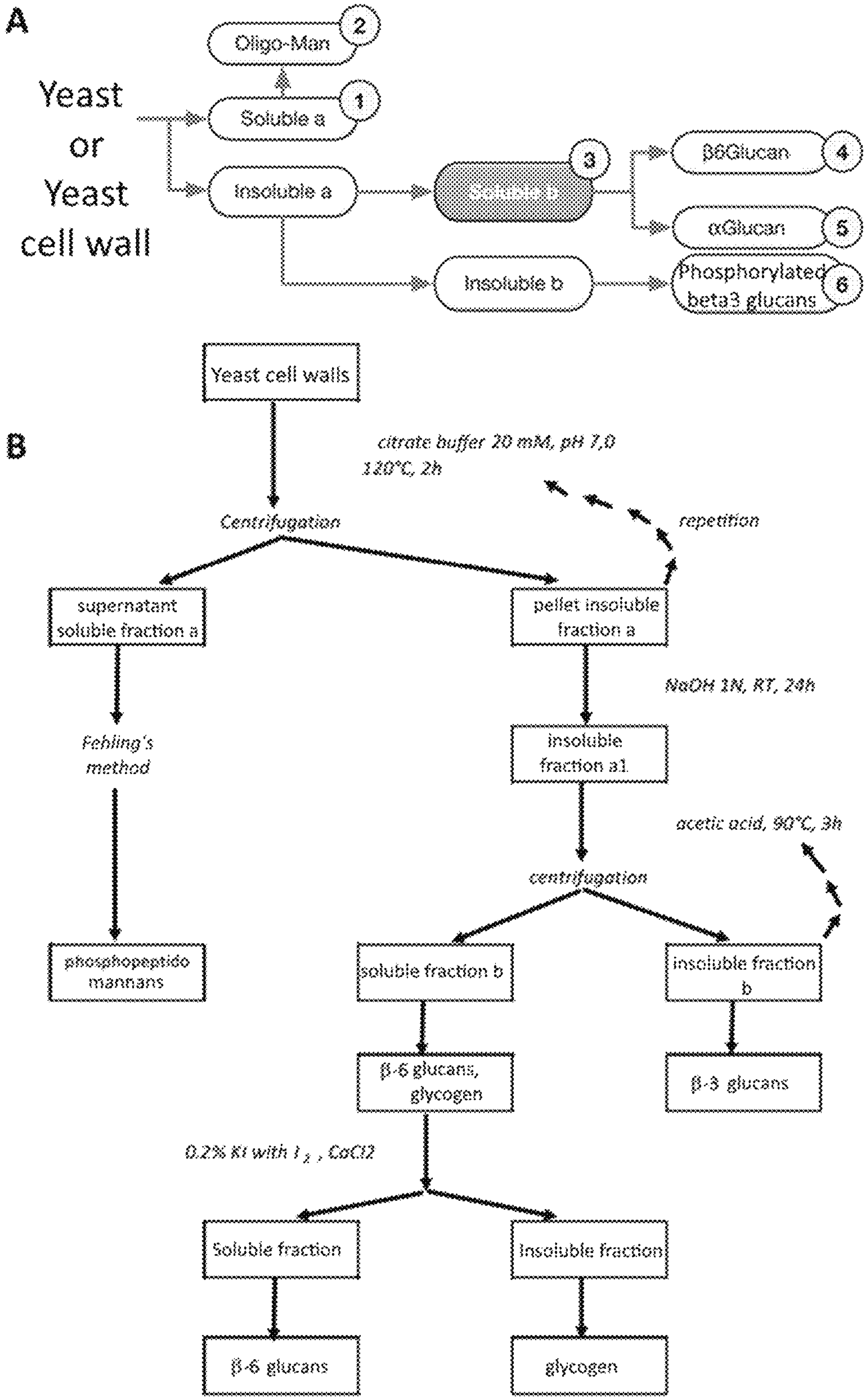

[Fig. 2]
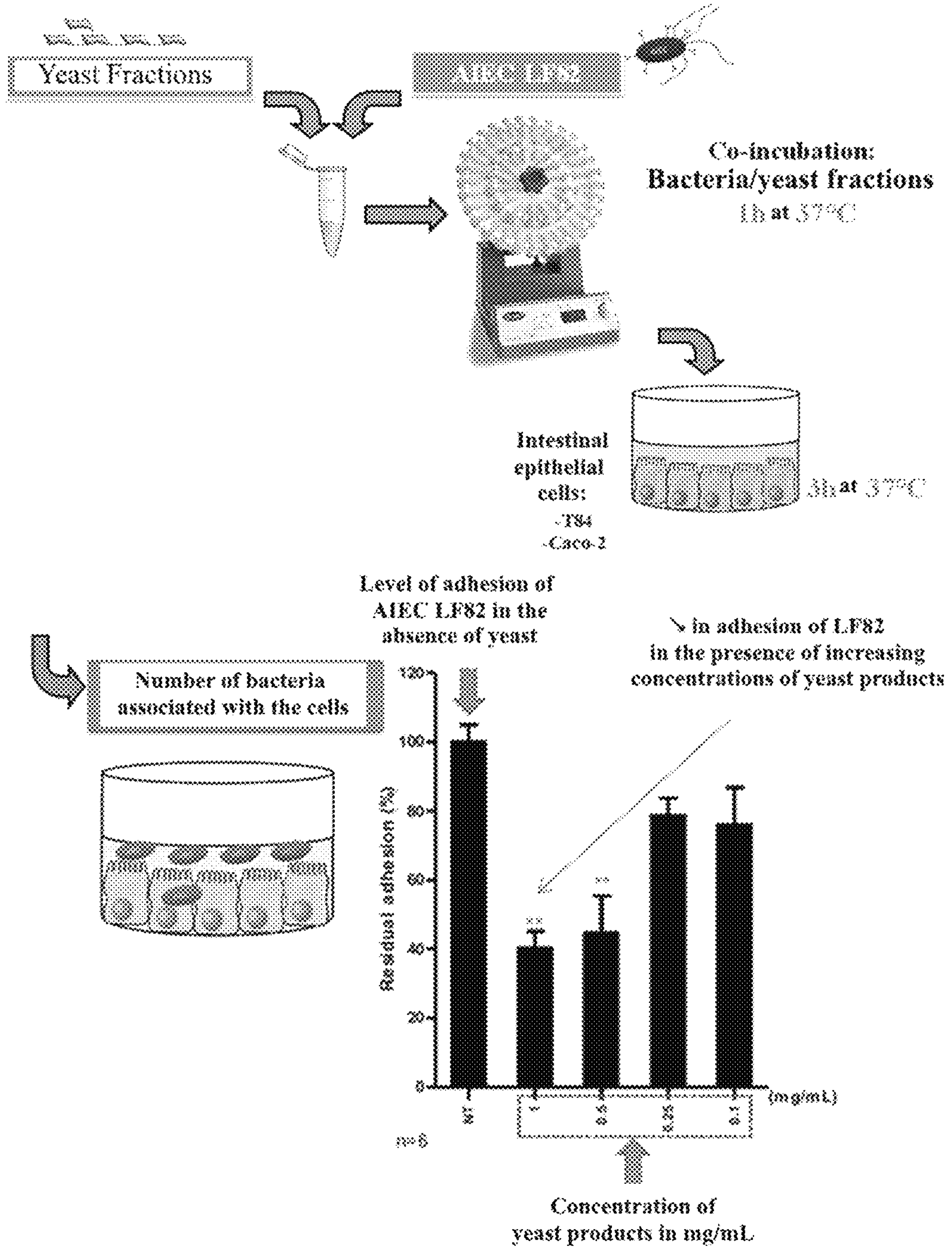

[Fig. 3]
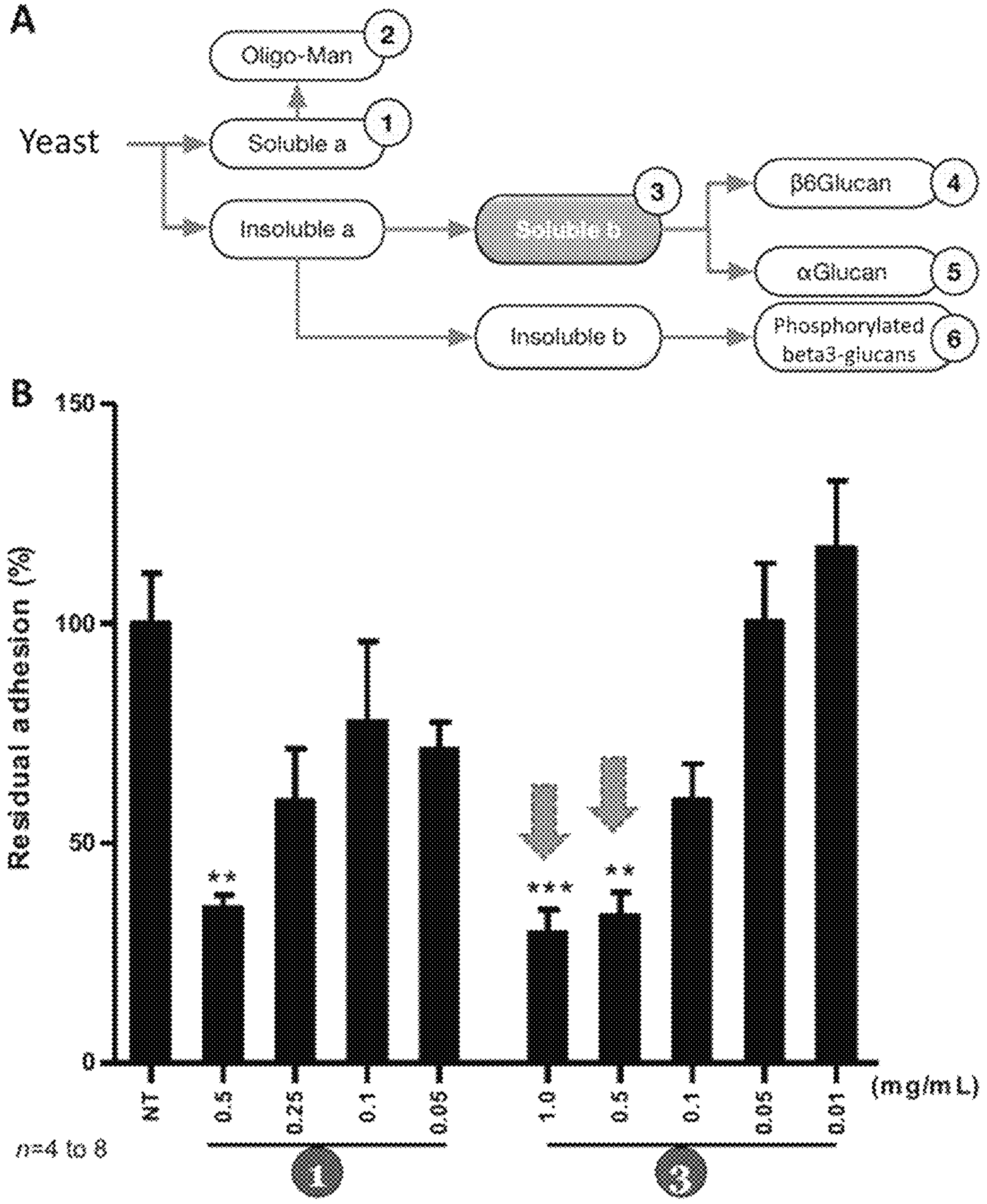

[Fig. 4]
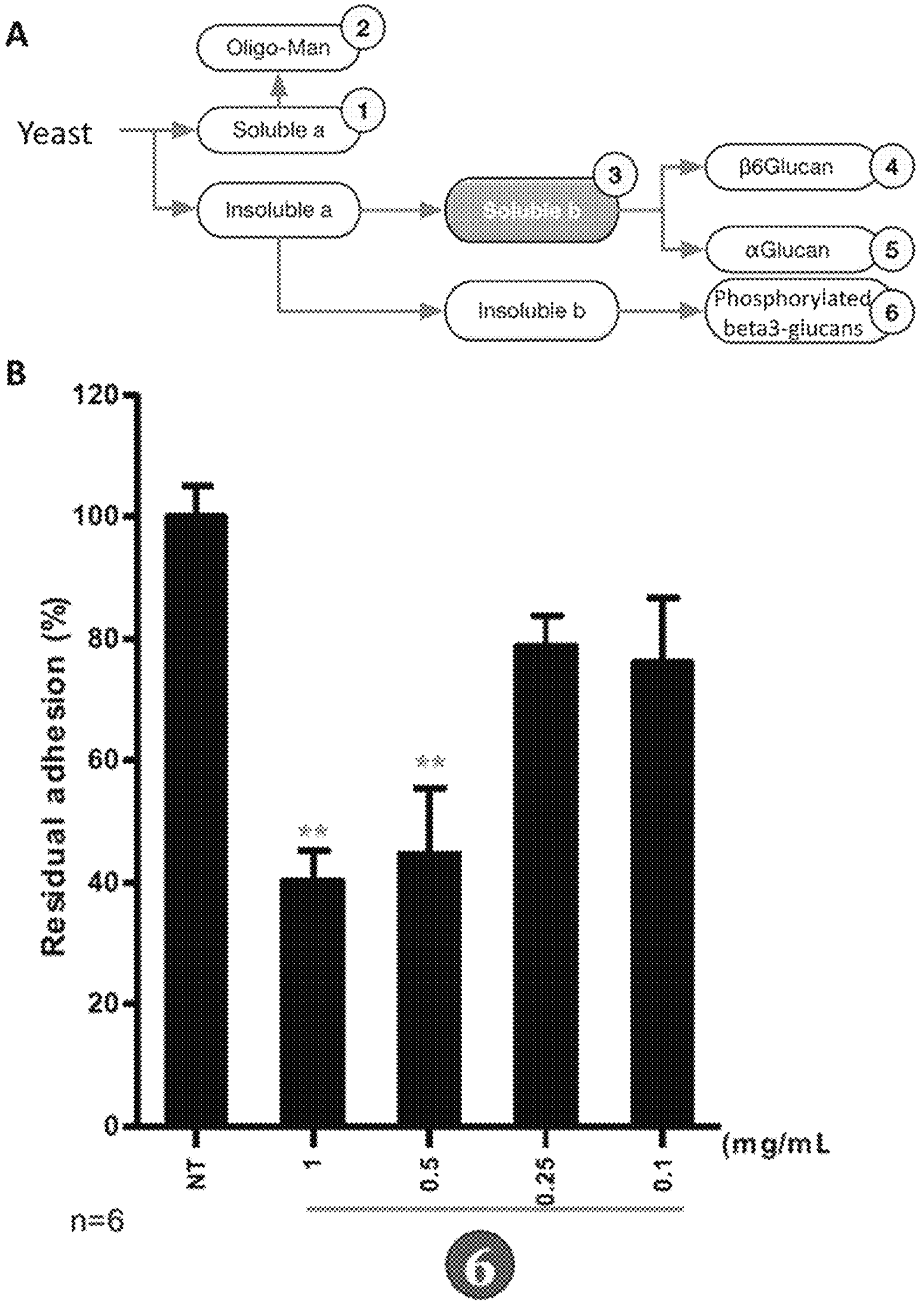

[Fig. 5]
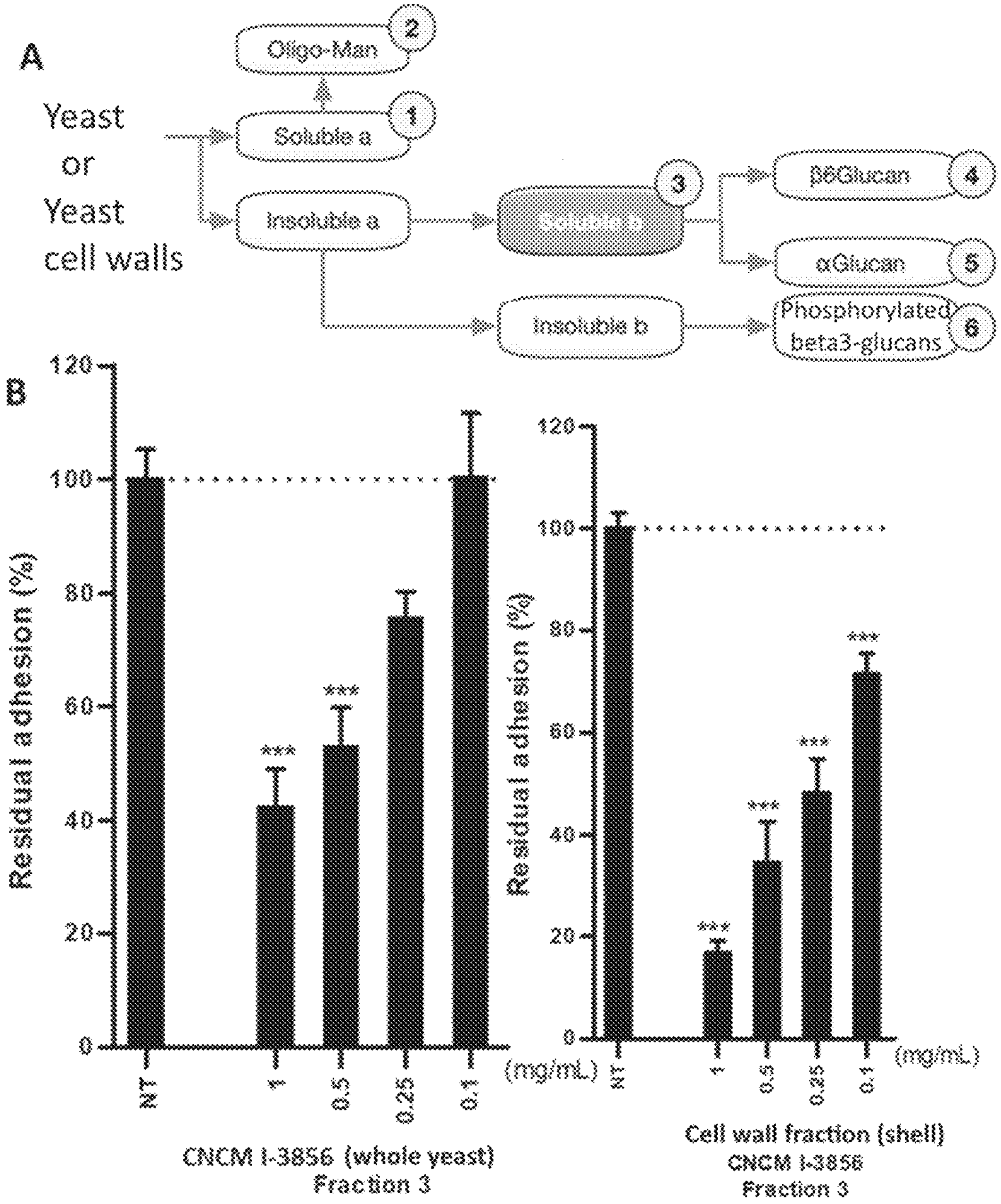

[Fig. 6]
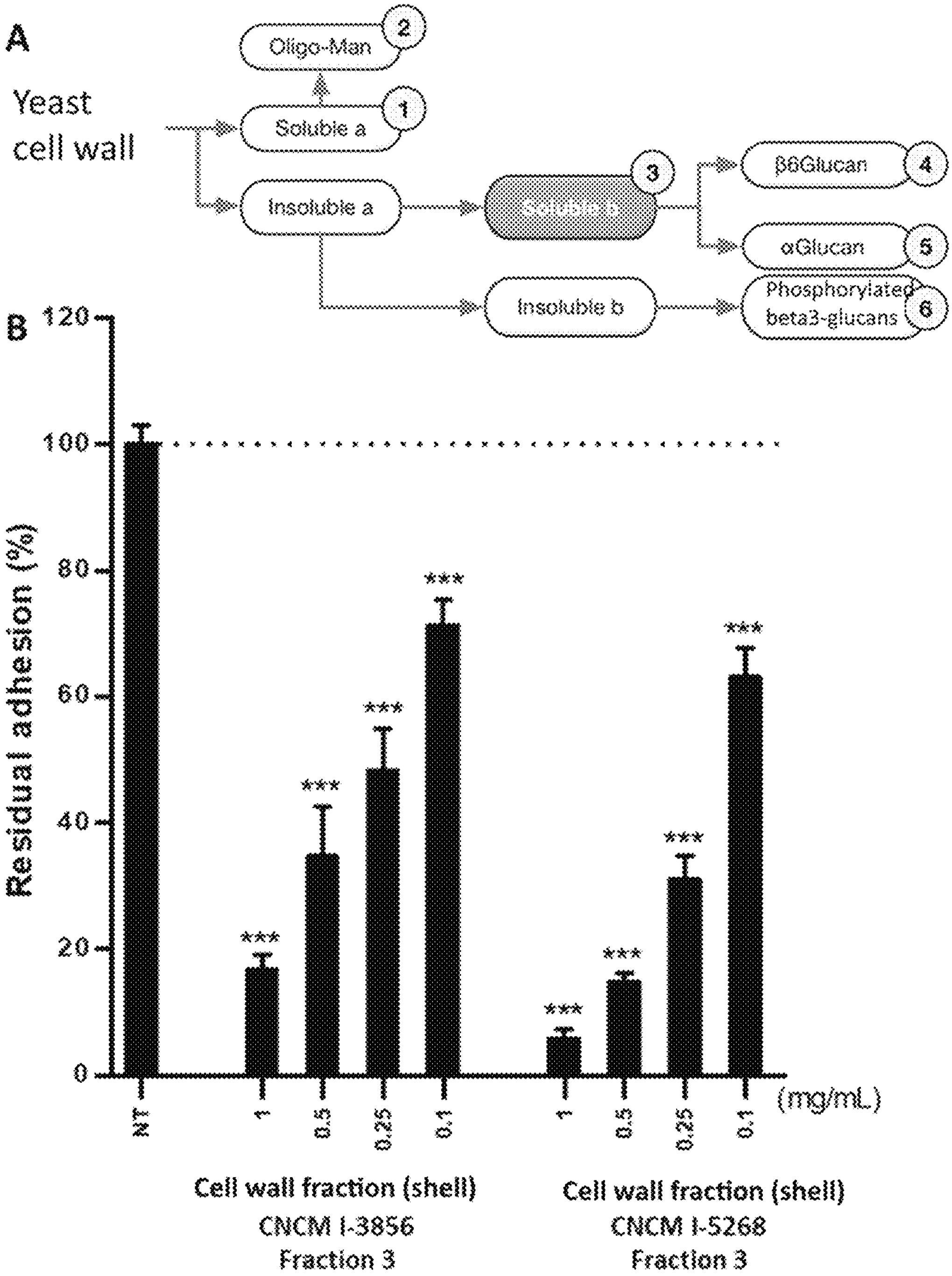

[Fig. 7]
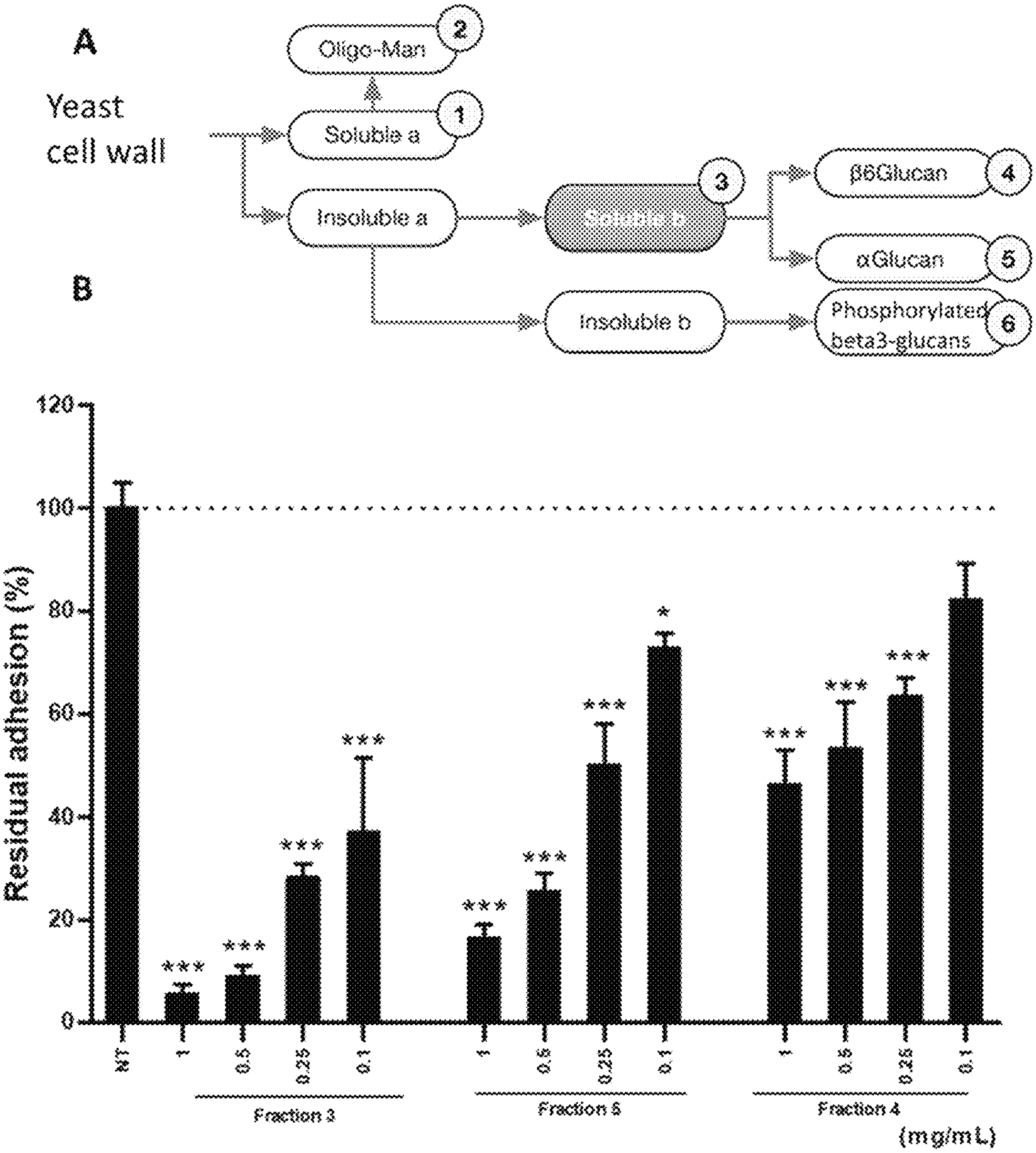

[Fig. 8]
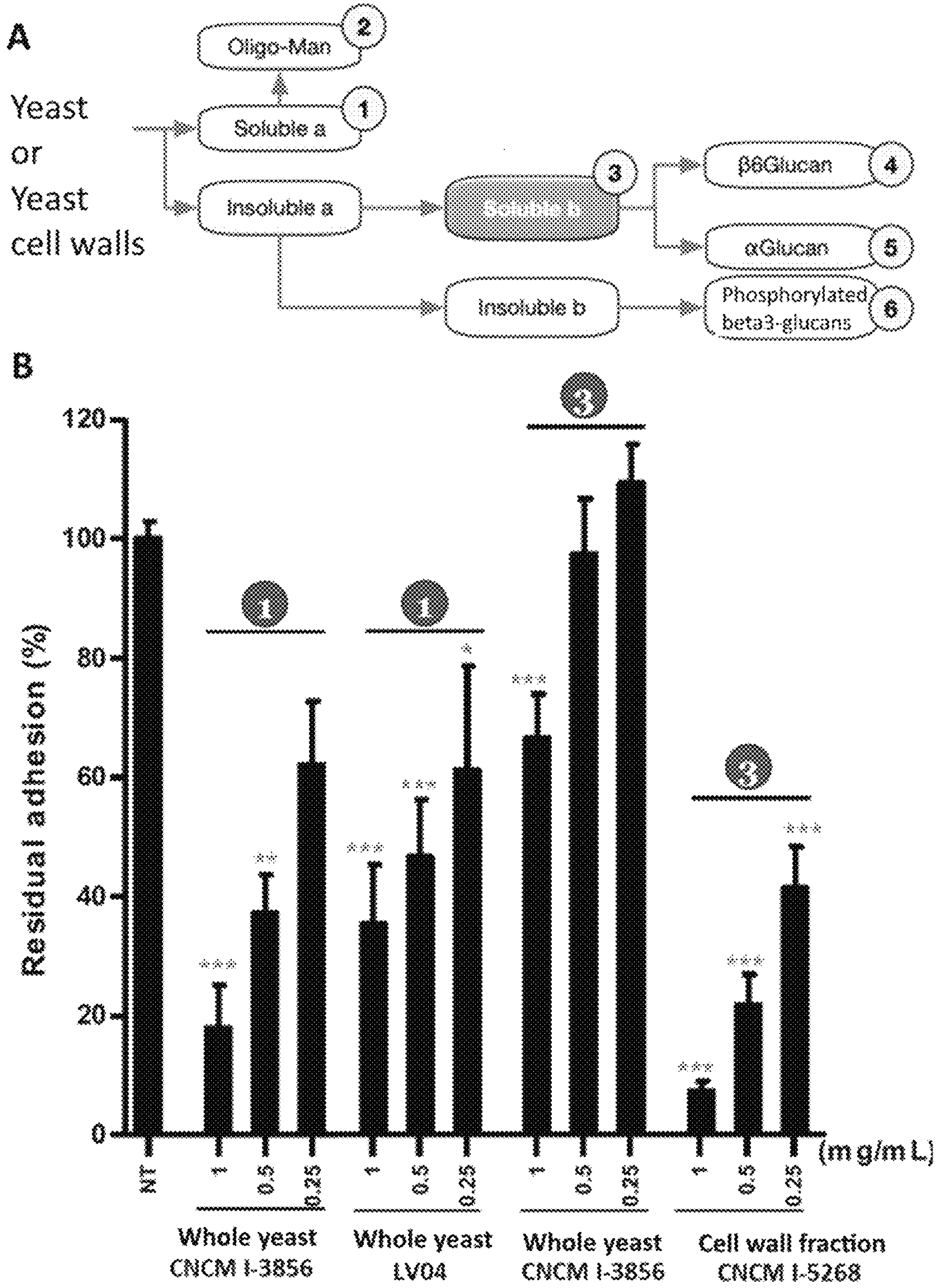

[Fig. 9]
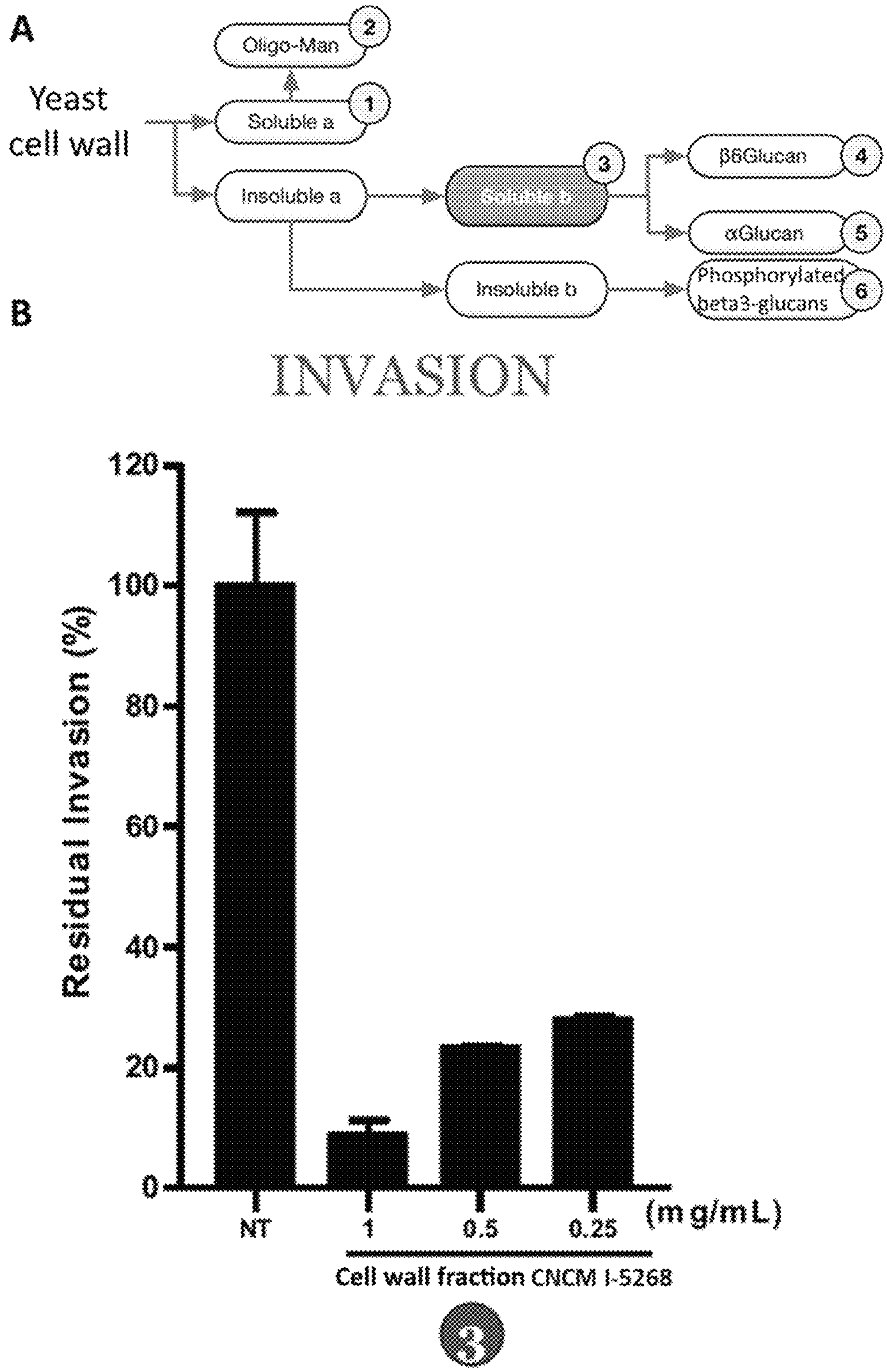

[Fig. 10]
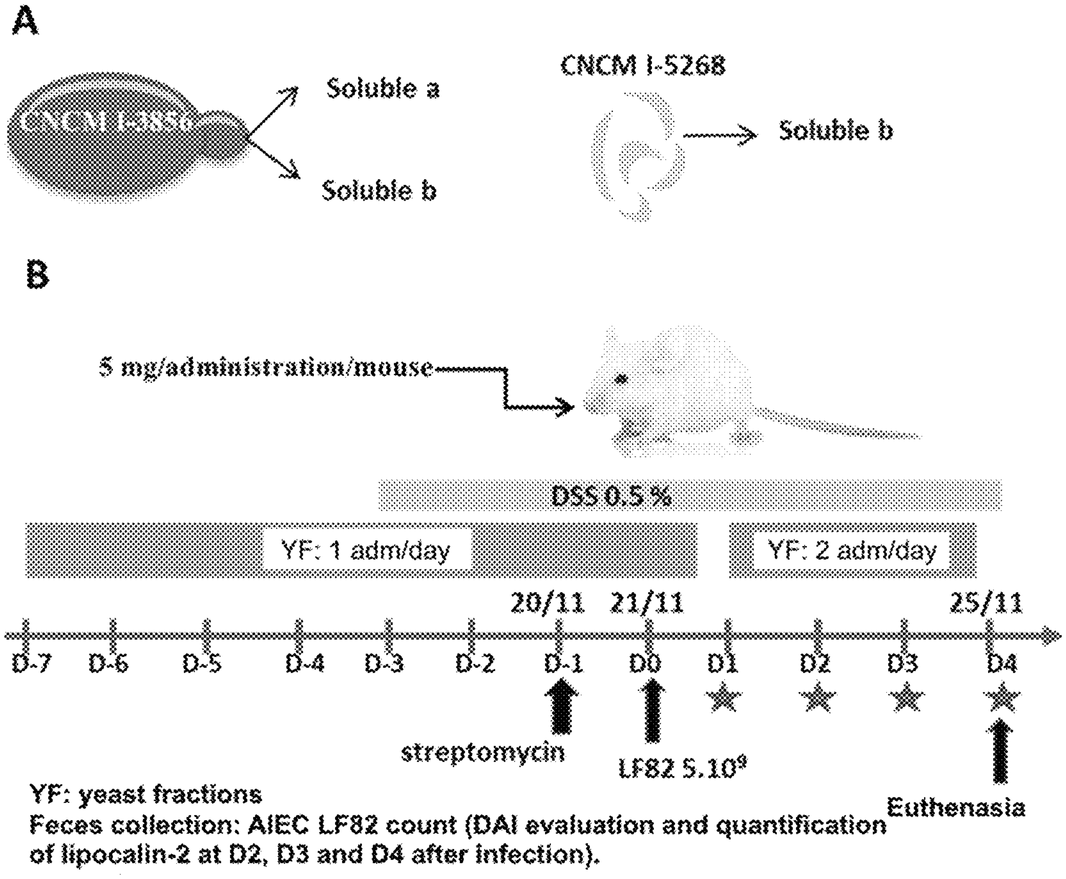

[Fig. 11]
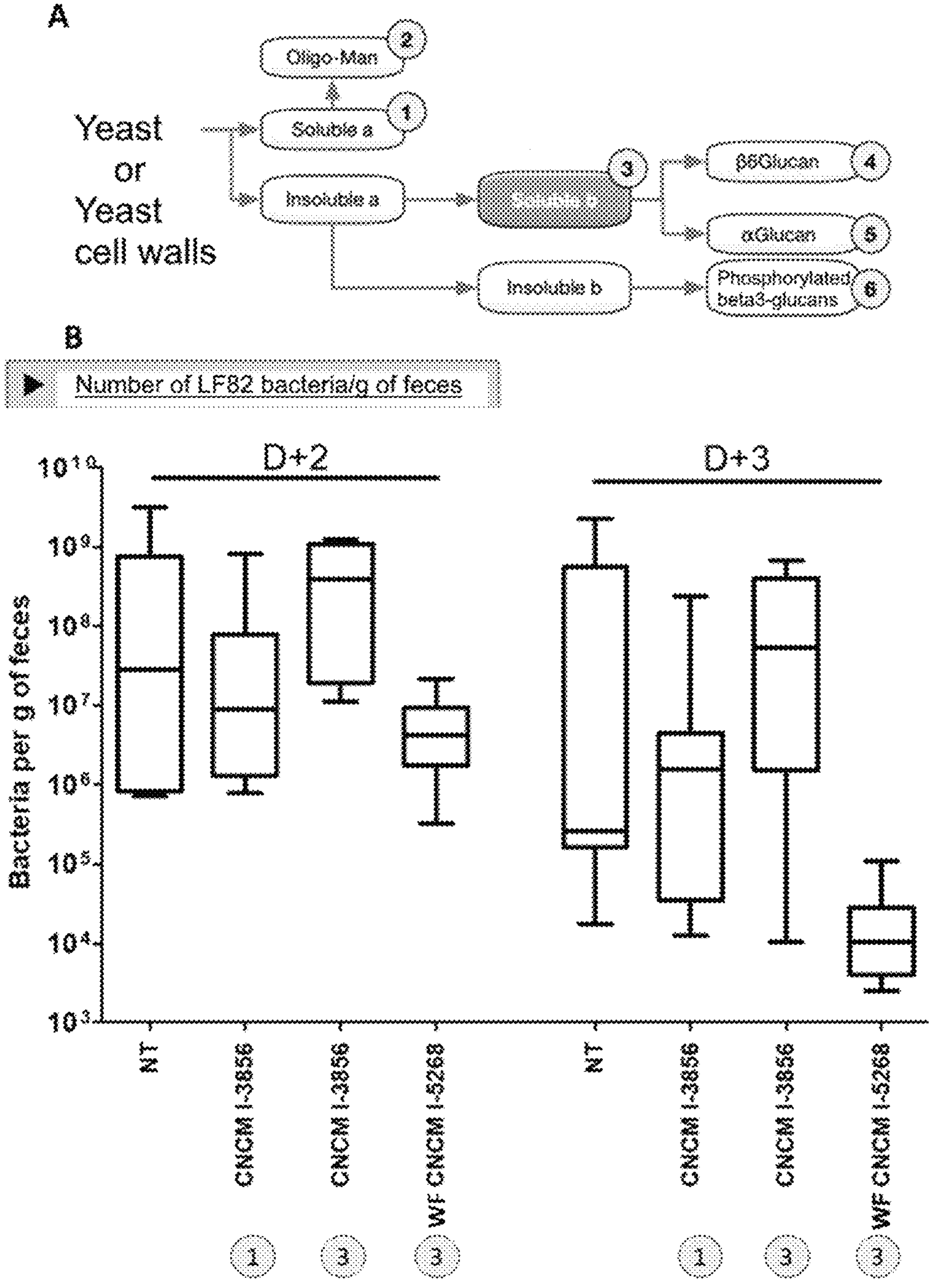

[Fig. 12]
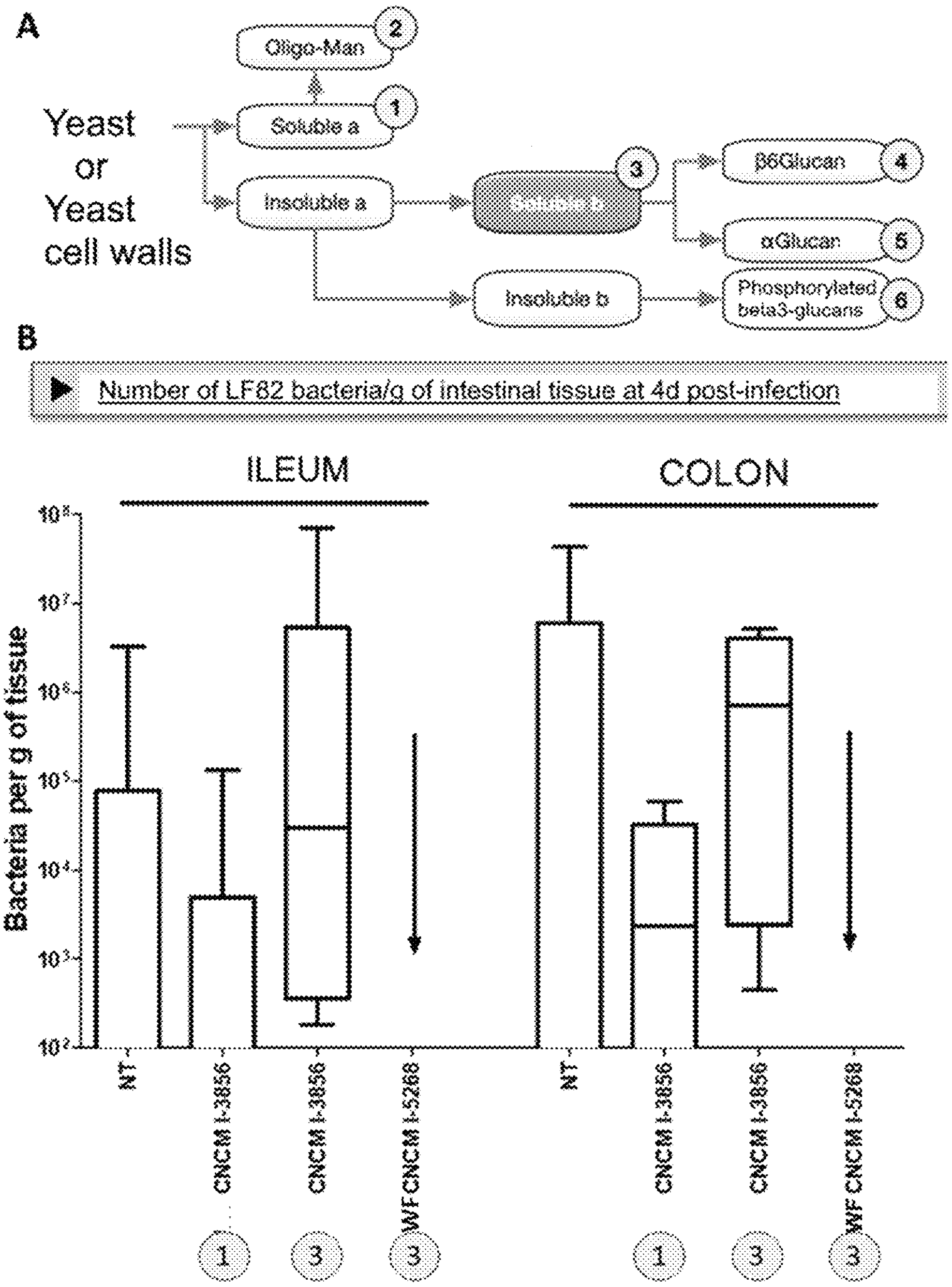

GLYCOSIDE INHIBITORS OF YEAST

FIELD

This disclosure relates to a method for obtaining a composition of yeast cell wall polysaccharides and to its use for the treatment of gastrointestinal pathologies or for the preparation of food supplements aimed at improving intestinal comfort.

BACKGROUND

An imbalance in pro-inflammatory and anti-inflammatory bacterial species of the microbiota, as well as the predominance of certain families of bacteria (Enterobacteriaceae, Fusobacteria) or the rarity of other species (*Clostridia, Faecalibacterium*), have been described in people who have chronic inflammatory bowel disease (CIBD). Specialized strains of *Escherichia coli* (*E. coli*) are also responsible for diarrhea, food poisoning, urinary tract infections, septicemia, and meningitis (Kaper J. B., Nataro J. P., Mobley H. L. —Pathogenic *Escherichia coli*, Nature Review Microbiology, 2004, 2, 123-140). In addition, many studies now support the concept in which the gut microbiota is a major environmental factor that can modulate the risk of colorectal cancer. Commensal bacteria of the microbiota could thus be directly pro-oncogenic. This is the case, for example, for certain strains of *E. coli* producing in vivo in the intestinal lumen a genotoxin called colibactin, which induces DNA damage to enterocytes similar to that induced by irradiation with ionizing gamma rays (Cuevas-Ramos G et al., "*Escherichia coli* induces DNA damage in vivo and triggers genomic instability in mammalian cells". PNAS USA, 2010, 107, 11537-11542).

Many microorganisms have already been described in the literature for their beneficial applications on the digestive tract in humans and for their nutritional value, as described for example in WO 2006/021965. These microorganisms are then commonly referred to by the term probiotics, which corresponds to living microorganisms capable of providing the host with health benefits when administered in sufficient quantity (Joint FAO/WHO Expert Consultation, Probiotics in food, FAO Food and nutrition paper No. 85, ISBN 92-5-105513-0).

More particularly, the use of *Saccharomyces cerevisiae* (*S. cerevisiae*) yeasts to treat pathologies associated with enterobacteriaceae is known. Thus, the earlier application FR 2 928 652 teaches that the yeast strain *S. cerevisiae* (CNCM I-3856, ScProl) is of therapeutic and prophylactic interest for the treatment of gastrointestinal pathologies associated with pathogenic microorganisms, in particular by limiting colonization and/or intestinal invasion by those microorganisms. In particular, administration of this yeast leads to a decrease in enterobacteriaceae in the colon. The results show that fractions rich in mannoproteins extracted from yeast strains (ScProl and/or SCB1) are able to inhibit in vitro the adhesion and invasion of human epithelial cells by strains of *E. coli* associated with Crohn's disease, one of the main CIBD (AIEC (Adherent Invasive *E. Coli*) strains). The study by Sivignon et al. (Inflamm Bowel Dis. 2015; 21(2):276-286) also teaches that cell wall compounds derived from the CNCM I-3856 strain reduce intestinal colonization by AIEC bacteria as well as the associated colitis symptoms in a mouse model mimicking Crohn's disease. Inhibiting the adhesion of AIECs to the intestinal wall results in a significant reduction in the invasion of AIECs into intestinal tissues and therefore their infectivity.

In recent years, increasing attention has been paid to glucans isolated from the cell wall of yeasts. Yeast cell wall glucans have thus been used to enhance or prime the immune response in humans and animals who have normal or diminished immunological function (G. Hetland. Curr. Med. Chem.-Anti-infective Agents 2003, 2:135; P. J. Rice, B. E. Lockhart, L. A. Barker, E. L. Adams, H. E. Ensley, D. L. Williams. Int. Immunopharmacol. 2004, 33:829). Patent application WO 2009/103884 teaches more particularly that yeast cell wall beta-glucans (in particular the CNCM I-3856 strain) limit intestinal inflammation. Jawahara et al. (PLoS One 2012; 7(7):e40648) further discloses that the beta-glucan fractions of *S. cerevisiae* yeasts (in particular the LYSC 318.2 strain) are capable of inhibiting the pathogenic action of *Candida albicans*. Finally, Pengkumsri et al. (Food Sci Technol, Campinas 2017, 31(1):124-130) discloses that beta-glucan fractions have immunomodulation properties that could be useful in the treatment of human colitis.

To the knowledge of the inventors, currently there is still no satisfactory curative treatment for CIBD. Surgery is sometimes considered, with excision of the injured portions of the small intestine, but this is a disabling operation with frequent relapses. Therefore, generally only the symptoms are treated, such as inflammation (through steroidal or non-steroidal anti-inflammatories and antibodies that target inflammatory cytokines) and chronic pain (typically through analgesics such as cannabinoids). In patients whose disease is progressive, doctors quickly institute immunomodulatory therapy to stop the attacks, prevent the appearance of new lesions, and prevent the risk of tumor development linked to chronic inflammatory conditions. However, these treatments also involve significant side effects in the medium and long term. Corticosteroids are thus being used less and less. It is therefore essential on the one hand to develop and improve existing prophylactic treatments, making it possible to improve intestinal comfort in healthy subjects, and on the other hand to prevent the development of pathologies in subjects at risk as well as to develop effective and better-tolerated therapies for patients suffering from gastrointestinal pathologies such as CIBD.

It therefore remains important to continue with innovative approaches in order to identify new solutions having increased effectiveness in improving the quality of life of patients suffering from gastrointestinal pathologies, in particular pathologies involving infectious agents. In particular, it would be quite relevant to identify new active ingredients or compositions having greater effectiveness in terms of an anti-adhesion and/or anti-invasive action.

SUMMARY

A composition of yeast polysaccharides comprising β-glucans and/or α-glucans and/or mannans is proposed, characterized in that said yeast polysaccharides are extracted from yeast cell walls. Typically, the β-glucans are β(1,6)-glucans. In some embodiments, the composition further comprises mannans and α-glucans. In particular, this patent application proposes a composition comprising from 5 to 25%, in particular from 10 to 20%, of α-glucans; from 30 to 50%, in particular from 35 to 45%, of β-glucans (in particular β6-glucans); and from 30 to 55%, in particular from 40 to 50%, of mannans. Typically, the yeasts are chosen among yeasts of the *Saccharomyces* genus. They can thus be chosen from the group comprising the strains deposited with the Collection Nationale de Cultures de Microorganismes (National Collection of Microorganism Cultures) under the numbers CNCM I-3799, CNCM I-3856, CNCM I-4407, CNCM I-4563, CNCM I-4812, CNCM I-4978, CNCM I-5128, CNCM I-5129, CNCM I-5268, and CNCM I-5269, and strain DBVPG 6763 deposited with the Collezione dei Lieviti Industriali (Industrial Yeasts Collection).

According to another aspect, a method is provided for obtaining a yeast composition comprising:

a) at least one step of fractionating (typically by hot incubation) a composition of yeast cell walls and collecting (extracting) an insoluble fraction (referred to as "insoluble fraction a"); and b) at least one step of extracting a soluble fraction (referred to as "soluble fraction b") from insoluble fraction a), said fraction containing β-glucans (in particular β6-glucans), preferably also mannans and generally α-glucans—this step typically comprises at least one step of incubating soluble fraction a) in a weak acid solution, and collecting (extracting) a soluble fraction ("soluble fraction b").

Typically, the method comprises a preliminary step of obtaining an insoluble yeast cell wall fraction.

The method preferably comprises a step al) of incubating the insoluble fraction a) in a strong base solution, after which the insoluble fraction (referred to as insoluble fraction a1) is collected. When this intermediate step is implemented, the fraction (or composition) incubated in the weak acid solution of step b) described above is then "insoluble fraction a1".

This disclosure also relates to a composition of yeast polysaccharides comprising β-glucans, mannans, and α-glucans as described in this patent application, in particular as obtained according to the method described herein, for its use in the treatment and/or prevention of gastrointestinal pathologies.

This invention lastly relates to a non-therapeutic use of a composition as defined in this disclosure, and in particular obtained according to the method described herein, for the preparation of a food composition intended to improve gastrointestinal comfort and/or to improve and maintain the homeostasis of the intestinal microbiota.

The features discussed in the following paragraphs may optionally be implemented. They may be implemented independently of each other or in combination with each other.

BRIEF DESCRIPTION OF DRAWINGS

Other features, details, and advantages will become apparent upon reading the detailed description below, and upon analyzing the appended drawings, in which:

FIG. 1: Diagrams illustrating the various protocols implemented. The top diagram (A) illustrates the extraction of the different yeast polysaccharide fractions from whole yeast or yeast cell walls. The bottom diagram (B) corresponds to the method of the invention in which the different yeast polysaccharide fractions are extracted from yeast cell walls.

FIG. 2 Diagram of the preincubation protocol on T84 and Caco-2 intestinal epithelial cells. The fractions extracted from yeasts are first incubated with AIEC bacteria then added to the cultures of intestinal epithelial cells organized into epithelium. The level of residual adhesion of bacterial strain AIEC LF82 is then estimated for decreasing concentrations of yeast fractions (1; 0.5; 0.25; 0.1 mg/mL).

FIG. 3 Residual adhesion levels (percentages) of strain AIEC LF82 to T84 cells (preincubation protocol) in the presence of "soluble fraction a" (also referred to as Fehling mannans because of the phosphopeptidomannan extraction protocol) (fraction 1, also called "soluble fraction a", or "soluble fraction b" (fraction 3) obtained from whole yeast strain CNCM I-3856 (means±SEM; :p<0.01, *: p<0.001, t-test).

FIG. 4 Residual adhesion levels (percentages) of strain AIEC LF82 to T84 cells (preincubation protocol) in the presence of 03-glucan-phosphate (fraction 6) obtained from whole yeast strain CNCM I-3856 (means±SEM; **:p<0.01, t-test).

FIG. 5 Residual adhesion levels (percentages) of strain AIEC LF82 to T84 cells (preincubation protocol) in the presence of "soluble fraction b" (fraction 3) obtained from whole yeast strain CNCM I-3856 or from CNCM I-3856 yeast cell walls (means±SEM; *:p<0.05; :p<0.01; *: p<0.001; t-test).

FIG. 6 Residual adhesion levels (percentages) of strain AIEC LF82 to T84 cells (preincubation protocol) in the presence of "soluble fraction b" (fraction 3) obtained from CNCM I-3856 yeast cell walls or from CNCM I-5268 yeast cell walls (means±SEM; *:p<0.05; :p<0.01; *:p<0.001; t-test).

FIG. 7 Residual adhesion levels (percentages) of AIEC LF82 cells to T84 cells (preincubation protocol) in the presence of "soluble fraction b" (fraction 3), α-glucans (fraction 5), or β6-glucans (fraction 4) derived from CNCM I-5268 yeast cell walls (means±SEM; *:p<0.05; ***: p<0.001; t-test).

FIG. 8 Residual adhesion levels (percentages) of strain AIEC LF82 to TC7/Caco-2 (preincubation protocol) in the presence of "soluble fraction a" (fraction 1) obtained from whole yeast strain CNCM I-3856 or yeast strain LV04, or "soluble fraction b" (fraction 3) obtained from whole yeast strain CNCM I-3856, or from CNCM I-5268 yeast cell walls (means±SEM; :p<0.01, *:p<0.001, t-test).

FIG. 9 Levels of residual invasion (percentages) of TC7/Caco-2 cells by bacterial strain AIEC LF82 (preincubation protocol) in the presence of "soluble fraction b" (fraction 3) derived from CNCM I-5268 yeast cell walls.

FIG. 10 Graph representing the in vivo administration protocol for yeast fractions (YF: yeast fraction) in mice (murine model of AIEC colonization). Yeast fractions are administered orally at a dose of 5 mg/mouse. Fractions tested: "soluble a" (fraction 1) obtained from whole yeast strain CNCM I-3856, or "soluble b" (fraction 3) obtained from whole yeast strain CNCM I-3856 or from CNCM I-5268 yeast cell walls.

FIG. 11 Estimation of the number of AIEC LF82 bacteria in the feces of mice 2 or 3 days after infection of the animals, as a function of the yeast fraction administered. The results are given as the number of AIEC bacteria/g of feces (box and whisker plot, min. to max.) (WF: cell wall fraction).

FIG. 12 Quantification of AIEC LF82 bacteria associated with the intestinal mucosa of treated or untreated mice, with yeast fractions, 4 days after infection. The results are given in the number of AIEC bacteria/g of tissue (box and whisker plot, min to max) (WF: cell wall fraction).

DETAILED DESCRIPTION OF EMBODIMENTS

The drawings and the following description for the most part contain elements that are certain in nature. Therefore not only can they serve to provide a better understanding of this disclosure, but where appropriate they also contribute to its definition.

"Approximately" in this application is understood to mean within a variation of 20%, in particular 15%, 10%, or 5%, relative to the numerical value indicated. As an example, the expression "a temperature of approximately 100° C." should be understood as a temperature of between 80 and 120° C., in particular between 85 and 115° C., more particularly between 90° C. and 110° C., and preferably between 95° C. and 105° C.

The inventors of this application have developed a new method which makes it possible to obtain a composition of yeast cell wall fragments, of which the effectiveness, in particular in inhibiting bacterial adhesion and invasion, particularly of adherent and invasive *E coli* bacteria (AIEC), is significantly increased in comparison to the whole yeasts or derivatives described in the prior art.

More particularly, the inventors have demonstrated, in a completely surprising manner, that a composition of yeast polysaccharides extracted from yeast cell wall fragments (also called yeast walls or cell walls) exhibits an adhesion- and bacterial invasion-inhibiting activity that is vastly superior to yeast polysaccharide compositions in which the polysaccharides are obtained from whole yeast. Also surprisingly, the yeast polysaccharide compositions according to the invention which in particular contain 01,6-glucans, and optionally mannans and α-glucans, also exhibit higher activity than the mannan fractions previously described. This result is unexpected, as it had been considered that the mannosidic structures exposed by glycoproteins expressed on the surface of enterocytes were exclusively responsible for the attachment to bacterial cells, via fimbrial structures (FimH) exposed on the surface of type 1 pili (Barnich et al. JCI, 2007).

The present disclosure therefore relates to a composition of yeast cell wall polysaccharides comprising β-glucans. Typically, the β-glucans comprise β(1,6)-glucans (also called 06-glucans below, particularly in the examples). Typically, said composition further comprises mannans and/or α-glucans.

A yeast cell is schematically composed of an envelope, also called shell or wall, and content. In the present application, the terms "parietal", "shell" or "wall" qualifying the polysaccharides or the yeast fragments described herein are thus used synonymously. The term "cell wall polysaccharides" thus means the polysaccharides that compose the wall (or shell) of the yeast.

Three main groups of polysaccharides form the yeast cell wall, in particular in *Saccharomyces cerevisiae* yeast: polymers of mannose (or mannans), representing about 40% of the dry mass of the yeast cell wall; polymers of glucose (β-glucan and α-glucan), representing about 60% of the dry mass of the cell wall; and polymers of N-acetylglucosamine (chitin), representing about 2% of the dry mass of the cell wall.

Glucans are polysaccharides composed of glucose monomers that may or may not be branched. They can be separated into different subtypes according to the mode of glucose binding. □-glucans are polymers of glucose monomers that are mainly linked together by □ □bonds (1-4).

Yeast β-glucans are polysaccharides composed of glucose monomers and can be divided into two subtypes according to the mode of glucose binding: long chains of about 1500 β-1,3-glucose units which represent about 85% of the yeast β-glucans, and short chains of about 150 β-1,6-glucose units which represent about 15% of the yeast β-glucans (Klis, F., Mol, P., Hellingwerf, K. and Brul, S. (2002) "Dynamics of cell wall structure in *Saccharomyces cerevisiae*". FEMS Microbiology Reviews 26, 239-256).

The short chains of β-1,6-glucans are involved in covalent bonds with β-1,3-glucan, mannoproteins, and chitin. These cross-links can also contribute to the modular structure of the cell wall (Kollar, R. et al. (1995) "Architecture of the yeast cell wall. β-(1,6)-glucan interconnects mannoprotein, β-(1,3)-glucan, and chitin". Journal of Biological Chemistry 270, 17762-17775).

The mannans are polymers or oligomers of mannoses which are associated via an N-glycan core. In particular, the *Saccharomyces cerevisiae* yeast mannans are polymers of α1,6 mannoses branched at α1,2 with terminal α1,3 (see in particular Sendid et al., Med Sci (Paris). 2009; 25(5):473-482). A fraction enriched in mannans according to this patent application comprises at least 30% mannans, in particular at least 35%, 40%, 50%, 55%, 60%, 65%, 70%, 75%, 80%, 85%, 90%, 95%, 99% mannans.

β6-glucan fraction is understood to mean a fraction enriched in β-1,6-glucan polysaccharides. Typically, such a fraction comprises at least 30% β-1,6-glucans, in particular at least 35%, 40%, 50%, 55%, 60%, 65%, 70%, 75%, 80%, 85%, 90%, 95%, 99% β-1,6-glucan polymers.

β3-glucan fraction is understood to mean a fraction enriched in 01,3-glucans. Typically, such a fraction comprises at least 30% β-1,3-glucan polymers, in particular at least at least 35%, 40%, 50%, 55%, 60%, 65%, 70%, 75%, 80%, 85%, 90%, 95%, 99% β-1,3-glucan polymers.

α-glucan (or glycogen) fraction is understood to mean a fraction enriched in α1,4 α1,6 glucans. Typically, such a fraction comprises at least 60% α1,4 α1,6 glucan polymers, in particular at least 65%, 70%, 75%, 80%, 85%, 90%, 95%, 99% α1,4-α1,6 glucan polymers.

Yeast polysaccharide compositions described in the prior art and typically obtained from whole yeast typically comprise 60-80% α-glucans, conventionally 65-75% α-glucans, 5-25% β-glucans, conventionally 10-20% β-glucans, and 5-25% mannans, conventionally 10 to 20% mannans.

The inventors have shown that the polysaccharide compositions obtained from yeast cell wall fractions are enriched in β-glucans, typically in 06 glucans, and preferably also in mannans. Without wishing to be tied to any theory, the inventors believe that the compositions obtained from a yeast cell wall fraction comprise heterogeneous polymers associated by strong, non-dissociable and typically covalent bonds, composed of alpha-glucans, beta-glucans (in particular beta-6 glucans), and mannans, as described above.

Thus, the yeast polysaccharide compositions of the invention typically comprise at least 30% β-glucans, in particular 30 to 50% β-glucans, preferably 35 to 45% β-glucans, in particular β(1,6)-glucans.

Preferably, the yeast polysaccharide compositions of this disclosure further comprise mannans. Typically, the compositions of this patent application are enriched in mannans and can comprise from 30 to 55% mannans, in particular from 40 to 50% mannans.

Preferably, the yeast polysaccharide compositions according to this disclosure comprise α-glucans, in particular from 5 to 25%, particularly from 10 to 20% α-glucans.

In certain embodiments, said compositions comprise the following proportions of polysaccharides:

5 to 25% α-glucans, preferably 10 to 20% α-glucans, 30 to 50% β-glucans, preferably 35 to 45% β-glucans, in particular β(1,6)-glucans, 30 to 55% mannans, preferably 40 to 50% mannans.

The walls (or shells) of yeast used in this application can be derived from one or more types of yeast. Yeasts are unicellular eukaryotic microorganisms belonging to the fungi kingdom. Yeasts particularly suitable for implementing this disclosure are yeasts of the *Saccharomyces* genus. These yeasts constitute a taxonomic genus of ascomycetes which do not form mycelium and include several species used in the food industry as fermentation agents. Conventionally, the yeasts belonging to the *Saccharomyces* genus can be chosen among food yeasts such as *S. cerevisiae, S. uvarum, S. bayanus*, or *S. pasteurianus*. The yeast is preferably a strain of the species *Saccharomyces cerevisiae* (brewer's or distiller's or baker's yeast, *S. cerevisiae* var. *boulardii*). For example, the *Saccharomyces cerevisiae* yeast strains deposited with the Collection Nationale de Cultures de Microorganismes under the numbers CNCM I-3799, CNCM I-3856, CNCM I-4407, CNCM I-4563, CNCM I-4812, CNCM I-4978, CNCM I-5128, CNCM I-5129, CNCM I-5268, and CNCM I-5269, are particularly well suited for this disclosure.

The compositions of this disclosure can be obtained from one or more yeasts of different strains or of different species.

The compositions of this disclosure are typically obtained from yeast wall preparations or yeast wall fragments separated from the cellular contents (cytoplasm), in particular by extraction of cell wall polysaccharides from yeast wall fragments. The methods for obtaining yeast walls or yeast wall fragments are well known in the technical field of this disclosure. Concerning this, one can consult the reference work "Yeast Technology", 2nd edition, 1991, G. Reed and T. W. Nagodawawithana, published by Van Nostrand Reinhold, New York, ISBN 0-444-31892-8.

Briefly, yeast cell wall fragments or yeast shell fragments can be obtained by lysis of the yeast cells that is chemical (solvents, acids, bases), physical (sonication, high pressure), enzymatic (typically the use of proteases and nucleases), or autolytic (endogenous enzymes), followed by separation of the soluble and insoluble parts, for example by physical means such as centrifugation and collection of the insoluble fraction (or part). Typically, centrifugation of the lysed yeast cell biomass yields a supernatant and a centrifugation pellet. The supernatant consists mainly of free amino acids and peptides resulting from protein degradation, and nucleotides resulting from nucleic acid (RNA, DNA) degradation. The centrifugation pellet contains the intact or partially degraded yeast walls in the form of yeast cells emptied of their contents.

Yeast autolysis is hydrolysis of the yeast's cell contents by its own enzymes. It is typically obtained by placing a suspension of yeast cells under certain physical medium conditions and/or in contact with activators causing apoptosis of the yeast cells and the release of its enzymes into the cell body. Hydrolysis of the cell contents produces soluble compounds. The insoluble fraction collected after the separation step constitutes the product called the yeast cell walls and includes the yeast cytoskeleton and the membranes and components not solubilized by autolysis or heterolysis. This insoluble fraction is often recovered in the form of an aqueous yeast cell wall suspension (or composition).

The yeast cell walls can be in liquid form (15-20% dry matter), dry form (more than 85% dry matter), or paste form (25-85% dry matter). The yeast cell walls are preferably presented in dry form. In some embodiments, wall fragments of CNCM I-5268 yeast are used as examples in the compositions and/or methods described herein.

For implementing the invention described herein, one can use yeast cell walls or shells or any composition containing them, originating from the same type of yeast or yeasts of different types (strains) or different species.

This disclosure also relates to a method for obtaining a composition of yeast cell wall polysaccharides as described above. Preferably, said method comprises in particular:

(a) at least one step of fractionating a composition of yeast cell walls and collecting an insoluble fraction, in particular at least one step of hot extraction, from a composition of yeast cell walls, an insoluble fraction (also called "insoluble fraction a" in the examples of this patent application), and (b) at least one step of extracting in a weak acid solution, typically a step of incubating "insoluble fraction a" in a weak acid solution, after which the soluble fraction (referred to as "soluble fraction b") is collected.

Typically, said method comprises a preliminary step, consisting of collecting a yeast cell wall fraction. In practice, this step is typically carried out by obtaining an insoluble fraction from a yeast hydrolyzate (in particular a yeast autolysate), as described above. This step aims in particular to eliminate all or part (at least 60%, in particular at least 75%, more particularly at least 80%, at least 85%, at least 90%, and even more particularly at least 95%) of the compounds not associated or weakly associated with the wall (in this regard see the method for obtaining a yeast cell wall fraction described above).

Step a) of hot extraction (or hot hydrolysis) can be carried out by hot incubation of the yeast cell wall fragments in a solution, typically buffered to neutral pH, at a temperature above 75° C., in particular between 80 and 180° C., more particularly between 90 and 150° C., more particularly between 95 and 145° C. Typically at a temperature of approximately 120° C. Neutral pH is understood to mean a pH of approximately 7, in particular a pH of between 6 and 8. Hot incubation is typically maintained for a period of at least 30 minutes, in particular at least 1 hour, typically between 1 hour and 4 hours, or between 1 hour and 3 hours. Preferably, incubation is maintained for approximately 1.5 hours. The buffer solution is typically a solution based on citrate buffer (approximately 20 mM) or any other equivalent buffer solution in the field. After incubation, the soluble and insoluble fractions are separated, typically by centrifugation, and the insoluble fraction (insoluble a) is collected. Typically the centrifugation can be carried out at a speed of 4000 to 6000 rpm, preferably approximately 5000 rpm, for a duration of at least 20 min, in particular between 20 min and 40 min, preferably approximately 30 minutes. This step can be repeated between 2 and 4 times, preferably 2 times. The soluble fraction, collected at the end of this hot hydrolysis step, typically comprises phosphopeptidomannans, not strongly associated (typically non-covalently associated) with the cell wall polysaccharides.

The method preferably comprises a step a1) of extracting an insoluble fraction in a strong base solution, typically a step of incubating the insoluble fraction obtained at the end of step a) (referred to as "insoluble fraction a") in a strong base solution, at the end of which the insoluble fraction (referred to as "insoluble fraction a1" is collected. When this intermediate step is implemented, the fraction (or composition) incubated in the weak acid solution of step b) described above is then "insoluble fraction a1".

Step a1) of extracting in a strong base solution typically includes a step of incubating insoluble fraction a) in a strong base solution. The strong base solution is typically a solution of sodium hydroxide (NaOH) or any other equivalent, preferably concentrated to about 1N. Incubation in the strong base solution is typically carried out at room temperature, preferably between 16 and 24° C., in particular at about 20° C. It is ideally carried out while stirring for a period of at least 16 hours, typically between 16 hours and 32 hours and preferably 24 hours. The soluble and insoluble fractions are then separated, typically by centrifugation, and insoluble fraction a1) is recovered. Typically the centrifugation can be carried out at a speed of 5000 to 8000 rpm, preferably approximately 7000 rpm, for a duration of at least 20 min, in particular between 20 min and 40 min, preferably approximately 30 minutes. The hot incubation steps follow the centrifugation. The inventors believe that this step allows eliminating residual phosphopeptidomannans.

Step b) of extracting in a weak acid solution typically includes a step of incubating "insoluble fraction a" or "a1" (if the intermediate step of extracting in a strong base has been implemented) in a weak acid solution. The weak acid solution is typically a solution of acetic acid or any other equivalent, preferably concentrated to approximately 0.5 N. The incubation in the weak acid solution is typically carried out at a temperature of at least 70° C., in particular between 75 and 130, more particularly between 75 and 115° C., more particularly at approximately 90° C. It is ideally carried out, preferably with stirring, for a period of at least 1 hour, typically between 2 and 4 hours and preferably 3 hours. The soluble and insoluble fractions are then separated, preferably by centrifugation, and the soluble fraction (referred to as soluble fraction b) is collected. Typically the centrifugation can be carried out at a speed of 4000 to 6000 rpm, preferably approximately 5000 rpm, for a duration of at least 20 min, in particular between 20 min and 40 min, preferably approximately 30 minutes. This step is repeated at least twice, in particular at least 3 times, 4 times, 5 times, 6 times, 7 times, 8 times, in particular between 3 and 8 times.

Typically the centrifugation steps of the method of this patent application are carried out at room temperature, preferably between 16 and 24° C., in particular at approximately 20° C.

Typically the "soluble fraction b" obtained according to the protocol described herein is a fraction enriched in β-glucans, in particular β-6 glucans, and preferably also in mannans (as defined above). Such a fraction also typically contains α-glucans. The method of the invention thus makes it possible to obtain a composition in particular as described above, and having the advantageous effects as claimed herein.

It should be noted that a β3-glucan fraction (i.e. typically enriched in beta-3 glucans as described above) can be obtained from yeast cell wall fragments (shells) according to this disclosure, when the insoluble fraction (also referred to as "insoluble fraction b") is collected at the end of step b). Similarly, this step b) can be repeated at least twice, in particular at least 3 times, 4 times, 5 times, 6 times, 7 times, 8 times, in particular between 3 and 8 times.

In certain embodiments, a fraction enriched with β6-glucans (preferably containing at least 60%, in particular at least 65, 70%, 75%, 80%, 85%, 90%, 95%, 99% β6-glucans) can be obtained from the soluble fraction obtained at the end of step b) ("soluble fraction b"). Thus, an isolated fraction of β6-glucans can for example be obtained by enzymatic treatment, typically with an amyloglucosidase (for example from *Aspergillus niger*). Preferably, however, the soluble fraction obtained at the end of step b) ("soluble fraction b") can be treated with an iodine solution (as illustrated in the examples). Incubation in the iodine solution is typically carried out at room temperature (preferably between 16 and 24° C., in particular at approximately 20° C.) (it is ideally carried out with stirring, for a period of at least 15 min, typically between 20 and 45 min, and preferably 30 min). After treatment with the iodine solution, the soluble and insoluble fractions are then separated, typically by centrifugation, and the soluble fraction (also referred to as "soluble fraction c") is collected. Typically the centrifugation can be carried out at a speed of 4000 to 6000 rpm, preferably approximately 5000 rpm, for a duration of at least 20 min, in particular between 20 min and 40 min, preferably approximately 30 minutes. An ethanol solution can then be added to the supernatant and the solution centrifuged under the same conditions as before. A concentrated solution of strong acid (typically a hydrochloric acid solution concentrated to at least 2N, preferably to about 3N) is added to the pellet to dissociate the β6-glucan and α-glucan complexes, then precipitated (in conventional manner with ethanol or any equivalent). This second method makes it possible to collect isolated β6-glucan and α-glucan enriched fractions (see also the methods described in the results).

As indicated above, the data obtained by the inventors have shown that the "soluble fraction b", obtained from yeast cell walls, very significantly inhibits the adhesion of type AIEC pathogenic bacteria, with the result of significantly reducing the invasion of AIEC (adherent invasive *E. coli*) bacteria in the intestinal tissues and therefore their infectivity. AIEC have also been shown to adhere to intestinal cells by binding to a mannose-rich glycoprotein known as CEACAM6. Thus, transgenic mice expressing the human CEACAM6 protein become very susceptible to AIEC infections although this pathotype is generally not very virulent against rodents. Treatment of mice infected with yeast strains or identified yeast derivatives has reduced colonization of the digestive tract by AIEC bacteria, thus validating the in vitro data.

Without wishing to be tied to any particular theory, the inventors believe that the "soluble fraction b", as described herein, comprises alpha (1-4) and (1-6) glucosidic units as well as mannosidic units which seem important for the presentation or the 3D conformation of the binding structures, such that such a fraction makes it possible to effectively inhibit the adhesion of bacteria to the intestinal wall.

This patent application thus relates to the use of a composition exhibiting an advantageous activity, as described herein, and/or obtained according to the method of this disclosure, as a medication. In particular, a composition as described herein is particularly suitable for the treatment or prevention of gastrointestinal pathologies or diseases. Said composition is typically a composition obtained from yeast cell walls, preferably of the *Saccharomyces* genus and enriched in β-glucans (in particular 06 glucans) and advantageously also in mannans. Preferably, said composition comprises at least 30% β-glucans and advantageously at least 30% mannans.

The terms "treatment" or "treating" as used herein, are defined as the administration of a composition as described herein to a patient in need thereof, for the purpose of curing, alleviating, remedying, improving, and/or affecting disease, and/or any symptom of disease, in particular gastrointestinal disease, a bowel disorder, or a functional bowel disorder. In particular, the terms "treating" or "treatment" indicate the reduction or alleviation of at least one undesirable clinical symptom associated with the disease, for example pain, inflammation, diarrhea, nausea or vomiting, loss of appetite, or fatigue. The terms "prevent" or "prevention" as used herein are defined as the administration of a composition as described herein to a patient in need thereof, with the aim of preventing the onset of a disease or of at least one of its symptoms and/or of reducing the severity of at least one of its symptoms.

In certain embodiments, the compositions of the invention can be used in clinical nutrition for the treatment or prevention of the pathologies described herein.

Patient is typically understood to mean a mammal and in particular a human being. In some cases, the patient may be in remission and the administration of a composition according to this patent application may be aimed at preventing or limiting relapses, in particular at reducing the severity of at least one of the symptoms of the disease or of the functional disorder in the event of relapse.

In certain embodiments, the composition of the invention is intended for veterinary use, typically for animal health. In such embodiments the patient is a non-human mammal, typically chosen among domestic or companion animals (such as cats or dogs) or livestock (ruminants, pigs, goats, sheep, horses, donkeys, etc.).

The gastrointestinal pathologies covered by this patent application may or may not be chronic, possibly associated with diarrhea or constipation. They typically include functional bowel disorders, infectious bowel diseases, colorectal cancer, and/or inflammatory bowel diseases.

Functional bowel disorders include in particular irritable bowel syndrome, functional abdominal distension, functional constipation, functional diarrhea, and any other unspecified functional bowel disorder (see in particular P. de Saussure & D Bertolini; Rev Med Switzerland 2006; volume 2.31649, *"Functional bowel disorders: contributions and limits of evidence-based medicine"*). Infectious bowel diseases typically include gastroenteritis, food poisoning, and/or diarrhea, of viral, bacterial, or parasitic origin. Chronic inflammatory bowel disease (CIBD) typically includes Crohn's disease and ulcerative colitis.

The compositions of this patent application are particularly useful for combating gastrointestinal colonization by pathogenic microorganisms, reducing adhesion to the intestinal mucosa, and even strengthening the intestinal barrier function against pathogenic microorganisms. Tests for inhibiting the adhesion of pathogenic microorganisms to intestinal epithelial cultures such as the T84 line, or to enterocytes obtained from intestinal biopsies of patients, with or without preincubation with the tested composition, are described in particular in the results of this application as well as in application WO 2009/103884 and the article by Sivignon et al. (IBD, 2015, vol 21(2):276-286).

As indicated above, infectious gastrointestinal pathologies, as well as CIBD and colorectal cancer, are generally associated with the presence of pathogenic microorganisms and/or an imbalance of the intestinal microbiota (dysbiosis) linked to the invasive nature of a specific pathogenic microorganism (see Rahmouni O, Dubuquoy L, Desreumaux P, Neut C. "Enteric microflora in inflammatory bowel disease patients". Med Sci (Paris). 2016 November; 32(11):968-973; Kaper J. B., Nataro J. P., Mobley H. L. —Pathogenic *Escherichia coli*), Cuevas-Ramos G et al., "*Escherichia coli* induces DNA damage in vivo and triggers genomic instability in mammalian cells". PNAS USA, 2010, 107, 11537-11542).

In general, it has been shown in this patent application that the compositions described herein are particularly useful for reducing adhesion to and invasion of gastric and/or intestinal mucous membranes and the associated inflammation, in particular for the pathologies listed above.

The pathogenic microorganisms targeted by the compositions described herein are typically intestinal pathogens, typically bacterial species of the Enterobacteriaceae family (such as *Salmonella* spp., *Klebsiella* spp., *Serratia* spp., or *Escherichia coli* (*E. coli*), bacteria of the Clostridioides *difficile* species, or yeasts of the *Candida albicans* species, advantageously bacteria whose adhesion to cells involves the type 1 pili adheson FimH. *E. coli* bacteria associated with colonic mucosa (mucosa associated *E. coli*) are preferably targeted, and in particular *E. coli* bacteria of the following types: AIEC (adherent-invasive *E. coli*), ETEC (enterotoxigenic *E. coli*), EIEC (enteroinvasive *E. coli*), EPEC (enteropathogenic *E. coli*), EHEC (enterohemorrhagic *E. coli*), EAEC (enteroaggregative *E. coli*), DAEC (diffusely adherent *E. coli*), UPEC (uropathogenic *E. coli*). In certain embodiments, colibactin-producing *E. coli* bacteria are of particular interest, in particular in patients suffering from colorectal cancer, having suffered from colorectal cancer, or at risk of developing colorectal cancer.

This patent application also relates to the non-therapeutic use of a composition as described above in the form of a nutraceutical, a food supplement, or a functional food aimed at improving or maintaining intestinal comfort and/or improving the intestinal flora (typically by limiting the intestinal colonization by pathogenic commensal bacteria). Improving or maintaining intestinal comfort is understood in particular to mean limiting or preventing intestinal bloating, limiting or preventing aerophagia, and/or regulating digestion, in humans or animals.

A composition according to this patent application may comprise, in addition to the active fraction extracted from yeast cell walls (composed of the polysaccharide cell wall fraction as described above and preferably obtained according to the described method), any excipient, carrier, and/or adjuvant conventionally used in the pharmaceutical field, or for the formulation of a food supplement, nutraceutical, or functional food, and which is chemically compatible with said active fraction (i.e. β-glucans, mannans, and yeast cell wall α-glucans, in particular the "soluble fraction b" illustrated as an example). For example, a composition of the invention may comprise components chosen among vitamins, trace elements, amino acids, and other additives intended for nutrition and/or animal or human health.

Functional food or nutraceutical are understood to mean a food that contains ingredients having beneficial health effects or capable of improving physiological functions, in particular herein for digestive well-being. Food supplement is understood to mean a foodstuff intended to supplement the normal diet, in accordance with EU Directive 2002/46/EC. A food supplement constitutes a concentrated source of nutrients or other substances having a nutritional or physiological effect, when taken alone or in combination, in small quantities. Foodstuffs intended for specific nutrition is understood to mean a food with a specific nutritional objective, intended for a well-defined population group, such as infants, young children, or athletes.

Physiologically acceptable adjuvants, vehicles, and excipients are typically described in the "Handbook of Pharmaceutical Excipients", second edition, American Pharmaceutical Association, 1994. To formulate a pharmaceutical composition according to the present invention, those skilled in the art can also advantageously refer to the latest edition of the European Pharmacopoeia or the United States Pharmacopoeia (USP). Commonly used carriers, excipients, and adjuvants include, but are not limited to, saline solutions, solvents, dispersing media, coatings, preservatives, antibacterial and antifungal agents, isotonic agents, and absorption-delaying agents.

The composition may be used as a drug or as an active ingredient, or in a context of non-therapeutic use, typically as a dietary supplement. The formulation and dosage of the active fraction are then adapted to the chosen use.

In the context of therapeutic use, the composition may be formulated for oral or enteral administration.

In the context of a pharmaceutical composition or a food supplement, the composition of the food according to this invention may be in different dosage forms, such as liquid form or in the form of a capsule, sugar-coated tablet, pill, powder, suppository, or any other dosage formulation. As a functional food, the composition of the foods according to this invention may be presented in a wide variety of food and drink forms, for example juices or milk-based preparations.

EXAMPLES

Materials and Methods

Method for the Extraction of "Soluble Fraction a" Phosphopeptidomannans by Fehling's Solution:

1. 50 g of yeast were suspended in 300 mL of 0.02 M citrate buffer (pH 7), sterilized in an autoclave at 121° C., 90 min.
2. Centrifuge at 5000 rpm at 4° C., 30 min. Collect the supernatant.
3. Suspend pellet in 300 mL of 0.02 M citrate buffer, once again autoclave at 121° C., 90 min. Then centrifuge again to separate supernatant and pellet.
4. Combine the two supernatants together (X mL).
5. Put the same volume of Fehling's solution (X mL) in the supernatant, stir at 4° C. overnight. Precipitates will form. The phosphopeptidomannan-copper complex is grey-blue. Collect the precipitate by centrifugation at 5000 rpm, 4° C., for 30 minutes.
6. Add 100 mL of 3N HCl to the precipitates, then stir at 4° C. until the precipitates dissolve. The copper complex decomposes, and the solution turns green.
7. Add 300 mL of ethanol to precipitate the phosphopeptidomannans, stir at 4° C. overnight. Collect the precipitate (white color) by centrifugation at 5000 rpm, 4° C., for 30 minutes.
8. The phosphopeptidomannan precipitates are dissolved in 50 mL of water. Dialyze (MWCO 3500) against water overnight at 4° C. Then dry and freeze-dry the dialyzed mannans.

Preparation of Fehling's Solution (Mix Freshly Used Buffers A and B)

Buffer A 1. 35 g Copper(II) sulfate. $5H_2O$ is dissolved in 300 mL of $H_2O$
2. Add 5 mL of 2 N sulfuric acid
3. Add water to 500 mL Buffer B (Corrosive)

1. 77 g sodium hydroxide+175 g sodium potassium tartrate
2. Add $H_2O$ to 500 mL.

Reference: Method for Fingerprinting Yeast Cell Wall Mannan (1969) Journal of Bacteriology, v.100, p 1175.

Obtaining "Soluble Fraction b": Separation of β1,3 Glucans and β1,6 Glucans (with Glycogen i.e. α-Glucans) by a Hot Dilute Acetic Acid Solution:

1. Collect the pellet obtained from 50 g of whole yeast or a yeast cell wall fraction (insoluble fraction after extraction in a hot citrate buffer, also called "insoluble fraction a") in 1 L of 1N NaOH solution, then stir at room temperature for 24 hours, to eliminate phosphopeptidomannan residues.
2. Collect the pellet (insoluble fraction a1) after centrifugation at 7000 rpm at 4° C. for 30 minutes. Wash the pellet with 1 L of water, centrifuge again, and save the pellet.
3. Extract the pellet with 800 mL of 0.5 N acetic acid, stir at a temperature of 90° C. for 3 hours.

Allow to cool then centrifuge at 7000 rpm at 4° C. for 20 min. Save the supernatant and the pellet. The pellet is extracted again with 800 mL of 0.5 N acetic acid, while stirring at 90° C. for 3 hours, followed by a new centrifugation.

4. Repeat step 3 at least 5 times until 5 L of supernatant has been collected (mainly composed of glycogen and β6-glucans, also called "soluble fraction b"). Neutralize the supernatant with a NaOH solution, concentrated by water evaporator. Then dialyze (MWCO 3500) against water at 4° C. overnight. The obtained fraction constitutes soluble fraction b. Analysis of this fraction demonstrates that it contains 3-6 glucans, α-glucans (glycogen), and mannans strongly bound (i.e. not dissociated by the hot extraction step) to the glucan polymers.
5. Dialyze the pellet (mainly composed of 03 glucan) against water at 4° C. overnight.
6. Freeze-dry the dialyzed samples.

REFERENCES

1. The structure of b(1→3)-D-glucan from yeast cell walls (1973) Biochem J, v.135, p 19.
2. Refinement of the structures of cell-wall glucan of *Schizosaccharomyces pombe* by chemical modification and NMR spectroscopy (2004) Carbohydrate Res., v.339, p 2255.

Separation of Glycogen and β6-Glucans

1. A 500 mg quantity of a composition of "soluble fraction b" is added to 50 mL of a working solution. Stir, then allow to stand at room temperature for 30 minutes. Red-brown granules are formed (glycogen-iodine precipitates).
2. Centrifuge at 5000 rpm for 30 min at room temperature. Save the supernatant and the pellets. Add 50 mL of working solution to the supernatant, then 100 mL of ethanol, stir at room temperature for 30 min.
3. Centrifuge again. Combine the granules (pellet 1, mainly Glycogen) into a single fraction. Add an additional 600 mL of ethanol to the supernatant, stir at room temperature for 30 minutes. Light yellow granules are formed.
4. Centrifuge to collect the granules (pellet 2, primarily 06-glucan).
5. To dissociate the iodine from the glycogen, add 100 mL of 3N HCl to pellet 1, stir until pellet 1 is dissolved (brown solution). Then add 300 mL of ethanol, and stir for 30 min at room temperature. Black-purple granules are then formed. Centrifuge and save the pellet. Then add an additional 100 mL of 3N HCl to dissolve the tablet. Add another 300 mL of ethanol, and stir for 30 min at room temperature so that white balls form. Centrifuge and save the granules (pellet 3, Glycogen).
6. Respectively dissolve pellets 2 and 3 in 50 mL of water. Then dialyze against water, 4° C., overnight.
7. Freeze-dry the dialyzed samples.

Preparation of the Working Solution (Iodine):

1. 4.35 g of iodine and 43.5 g of potassium iodide in 166.5 mL of water
2. Add 10.5 mL of a saturated $CaCl_2$) solution.

Reference: Methodologies of tissue preservation and analysis of the glycogen content of the Broiler chicken liver (2007) Poultry Science, v.86, p. 2653.

Yeasts Used:

CNCM I-3856: live *Saccharomyces cerevisiae* yeast deposited under number CNCM I-3856;

LV04 *Saccharomyces cerevisiae* whole brewer's yeasts (Lesaffre internal collection)

Cell wall fraction (shells) of yeast CNCM I-3856 (FP I-3856)

Cell wall fraction (shells) of yeast CNCM I-5268 (FP I-5268).

Fractions tested, obtained from compositions of whole yeast(s) or of yeast cell walls (cell wall fraction):

soluble b

β6-glucans glycogen

β3-glucan phosphates phosphopeptidomannans (also called Fehling phosphopeptidomannans or "mannans").

Protocols for Preincubation (See FIG. 2):

Adhesion test: The tests were carried out on T84 or Caco-2/TC7 cells seeded at $1.5\times10^5$ cells/well in a 48-well plate and incubated for 48 hours at 37° C. in an atmosphere containing 5% $CO_2$. AIEC LF82 bacteria at $1.2\times10^7$ CFU/mL were incubated for 1 hour, on a Stuart® orbital shaker at room temperature, with increasing concentrations of the yeast sample (1:1 ratio). After 48 hours of culture, the cells were infected with the bacteria/yeast extract mixture for 3 hours at 37° C. in an atmosphere containing 5% $CO_2$. Cells were infected with a multiplicity of infection of 10 bacteria/cell. The average adhesion rates (which come from at least 3 independent experiments) were expressed as a percentage of residual adhesion, which is the ratio between bacterial adhesion in the presence of yeast and adhesion in the absence of yeast, is considered to be 100%. Error bars correspond to the standard error of the mean or SEM.

Invasion test: the protocol is identical to that of the adhesion test; however, after the 3-hour incubation period, the cells are incubated for 1 hour with gentamycin (100 μg/mL) in order to eliminate extracellular bacteria and only count invasive bacteria.

Results:

Initially, all fractions were tested in a protocol of adhesion to T84 cells. Additional tests were then performed on Caco-2/TC7 cells and in an invasion protocol.

As illustrated in FIG. 3, the "soluble a" (phosphopeptidomannan) fraction from CNCM I-3856 whole yeast significantly inhibits the adhesion of AIEC bacteria to T84 epithelial cells. Surprisingly, however, the "soluble b" fraction from this same whole yeast also exhibits significant inhibitory activity against the adhesion of AIEC bacteria.

FIG. 4 shows that the phosphorylated 03-glucan fraction from CNCM I-3856 whole yeast also significantly inhibits, although more moderately, the adhesion of AIEC bacteria to T84 epithelial cells.

FIG. 5 illustrates the comparison of the inhibitory activities against the adhesion of AIEC bacteria to T84 epithelial cells, of "soluble b" fractions obtained either from whole yeast (CNCM I-3856) or from the cell wall fraction of this same yeast. Although both exhibit significant inhibitory activity, the fraction obtained from the cell wall fraction exhibits greater activity than that obtained from whole yeast (residual adhesions at the dose of 1 mg/mL are 17% and 42% respectively). These different activities are correlated with different compositions of the "soluble b" fraction.

In order to verify that the obtained result was not linked to any cytotoxic activity of the sample, a cytotoxicity test was carried out with increasing doses of soluble fraction b. No cytotoxic effects were observed.

FIG. 6 illustrates a comparison of the inhibitory activities against adhesion of AIEC bacteria to T84 epithelial cells, of "soluble b" fractions obtained from two yeast cell wall fractions: CNCM I-5268 or CNCM I-3856. Very significant inhibitory activity is observed for these two fractions. As the residual adhesion percentages for equal doses are of the same order, this result strongly suggests that the increase in inhibitory activity is not directly linked to the strain used (CNCM I-5268 vs. CNCM I-3856) but rather to the production process. In other words, the "soluble b" fractions obtained from yeast cell wall fractions exhibit an inhibitory activity against the adhesion of AIEC bacteria to epithelial cells which is much greater than that observed for the "soluble b" fractions obtained from whole yeasts.

FIG. 7 illustrates the residual adhesion of AIEC LF82 bacteria to T84 epithelial cells, in the presence of "soluble b" fractions, glycogen or β6-glucans, obtained from CNCM I-5268 yeast cell wall fractions. The results show that the β6-glucans are less effective than the "soluble b" fraction and that the glycogen fraction has intermediate activity. The "soluble b" fraction is the most effective fraction.

FIG. 8 shows the residual adhesion (as a percentage) of AIEC LF82 bacteria to TC7/Caco-2 cells in the presence of mannan fractions (Fehling mannans) obtained from whole yeast (CNCM I-3856, or LV04), "soluble b" fractions obtained from CNCM I-3856 whole yeast or from the CNCM I-5268 yeast cell wall fraction. These new results confirm the results obtained previously with T84 cells, namely that "soluble b" fraction obtained from a yeast cell wall fraction has the greatest inhibitory activity.

FIG. 9 illustrates results showing a strong inhibition of the invasion of TC7/Caco-2 cells by AIEC LF82 bacteria preincubated with increasing doses of "soluble b" fraction obtained from cell wall fractions of CNCM I-5268 yeasts.

In Vivo Studies of the Activity of Yeast Fractions in CEABAC10 Transgenic Mice Infected with the AIEC LF82 Bacterial Strain.

Colonization of the intestinal tract by the AIEC LF82 strain was carried out in CEABAC10 transgenic mice expressing the human protein CEACAM6, acting as a receptor for AIEC bacteria in the context of Crohn's disease.

It has previously been shown (Sivignon et al. IBD, 2015) that CNCM I-3856 *S. cerevisiae* yeast extracts reduced colonization of the colon by the AIEC LF82 bacterium, thus leading to a reduction in colitis symptoms.

Preliminary results have now been obtained with the new fractions tested in vitro.

The protocol applied is illustrated in FIG. 10.

Briefly, yeast fractions were administered orally once daily from day −7 to day 0, and twice daily (5 hours apart) from day 1 to day 3. The fractions were solubilized in PBS at a concentration of 25 mg/mL (every day) and an amount of 0.2 mL/mouse was administered by gavage (5 mg/mouse). From day −3 to day +4, the mice received 0.5% DSS in drinking water. On day −1, the mice were treated p.o. with streptomycin (5 mg/mouse).

At the same time, LB (Luria Bertani) culture medium was inoculated (at 1/100th) with the AIEC LF82 bacterial strain and incubated at 37° C. while stirring until the exponential growth phase. After centrifugation, the bacteria were concentrated to $2.5\times10^{10}$ bacteria/mL. A quantity of 0.2 mL was then administered by gavage to the mice, i.e. $5\times10^9$ bacteria/mL.

The mice's weight and colitis symptoms were monitored for 4 days after infection. Feces were collected on days 1, 2, 3, and 4 post-infection in order to assess bacterial colonization.

The mice were euthanized on the fourth day after infection and the intestine was removed to assess the bacterial colonization associated with the mucosa (ileum+colon).

The fractions tested were as follows:

A: Untreated batch (n=10);

B: Soluble fraction a) of CNCM I-3856 whole yeast (n=8);

C: Soluble fraction b) of CNCM I-3856 whole yeast (n=8);

D: Soluble fraction b) obtained from CNCM I-5268 yeast cell wall fraction (n=8).

FIG. 11 shows the estimated number of bacteria in mouse feces two and three days post-infection, as a function of the yeast fraction administered. The results show that the quantity of bacteria in the feces is reduced by 25 in response to treatment with soluble fraction b) obtained from CNCM I-5268 yeast cell wall fraction compared to the untreated group, which confirms the excellent anti-adhesive properties of this fraction demonstrated in vitro in a pre-clinical model.

FIG. 12 shows the quantification of AIEC LF82 bacteria associated with the intestinal mucosa in mice treated or not treated with the yeast fractions, 4 days after infection. The results indicate the absence of bacteria in 100% of the mice treated with soluble fraction b) obtained from CNCM I-5268 yeast cell wall fraction, thus corroborating the results obtained in the feces.

The invention claimed is:

1. A method for obtaining a composition of yeast cell wall polysaccharides, comprising β(1,6)-glucans, wherein the method comprises the following steps:

i) a step of obtaining an insoluble composition of yeast cell walls, ii) at least one step of fractionating the insoluble composition of yeast cell walls obtained at the end of step i) and a step of collecting an insoluble fraction a., iii) optionally, a step of incubating the insoluble fraction a. obtained at the end of step ii) in a solution of a strong base and a step of collecting an insoluble fraction a1., and iv) at least one step of incubating the insoluble fraction a. obtained at the end of step ii) or the insoluble fraction a1. obtained at the end of step iii) in a solution of a weak acid and a step of collecting a soluble fraction b., said soluble fraction b. consisting of a composition of yeast cell wall polysaccharides comprising β(1,6)-glucan.

2. The method according to claim 1, wherein the method comprises a step of incubating the insoluble fraction a. obtained at the end of step ii) in a solution of a strong base and a step of collecting an insoluble fraction a1.

3. The method according to claim 1, wherein the yeast is chosen among yeasts 27. of the *Saccharomyces* genus.

4. The method according to claim 1, wherein the yeast is chosen among yeasts of the species *Saccharomyces cerevisiae.*

5. The method according to claim 4, wherein the yeast is obtained from any of the strains deposited with the Collection Nationale de Culture de Microorganismes under numbers CNCM I-3799, CNCM I-3856, CNCM I-4407, CNCM I-4563, CNCM I-4812, CNCM I-4978, CNCM I-5128, CNCM I-5129, CNCM I-5268, and CNCM I-5269.

6. A composition of yeast cell wall polysaccharides comprising β(1,6)-glucans, wherein the composition is obtained according to the method of claim 1.

7. The composition according to claim 6, wherein the composition comprises:

5 to 25% of α-glucans, 30 to 50% of β-glucans, and 30 to 55% of mannans.

8. The composition according to claim 7, wherein the composition comprises:

10 to 20% of α-glucans, 35 to 45% of β-glucans, and 40 to 50% of mannans.

9. A drug comprising the composition according to claim 6.

10. A veterinary composition comprising the drug according to claim 9.

11. A method of treating gastrointestinal pathologies associated with pathogenic microorganisms in a subject, comprising administering to a subject in need thereof an effective amount of the composition according to claim 6.

12. The method according to claim 11, wherein the pathogenic microorganisms are *Escherichia coli* bacteria associated with the intestinal mucosa (mucosa-associated *E coli*).

13. A method of treating gastrointestinal pathologies associated with pathogenic microorganisms in a subject, comprising administering to a subject in need thereof an effective amount of the composition according to claim 6.

14. The method according to claim 13, wherein the pathogenic microorganisms are *Escherichia coli* bacteria associated with the intestinal mucosa (mucosa-associated *E coli*).

15. A method of improving gastrointestinal comfort and/or improving intestinal flora in humans or animals, comprising administering to a human or an animal in need thereof an effective amount of the composition according to claim 6.

16. A method of improving gastrointestinal comfort and/or improving intestinal flora in humans or animals, comprising administering to a human or an animal in need thereof an effective amount of the composition according to claim 6.

* * * * *